United States Patent [19]
Hall et al.

[11] Patent Number: 6,095,977
[45] Date of Patent: Aug. 1, 2000

[54] METHOD AND APPARATUS FOR COLOR FLOW IMAGING USING GOLAY-CODED EXCITATION ON TRANSMIT AND PULSE COMPRESSION ON RECEIVE

[76] Inventors: Anne Lindsay Hall, 16015 W. Top-O-Hill Dr., New Berlin, Wis. 53151; Richard Y. Chiao, 10 Putnam La, Clifton Park, N.Y. 12065; David John Muzilla, 216 Eagle Lake Ave., Mukwonago, Wis. 53149

[21] Appl. No.: 09/048,487

[22] Filed: Mar. 26, 1998

[51] Int. Cl.[7] .................................................. A61B 8/06
[52] U.S. Cl. .......................................... 600/443; 600/455
[58] Field of Search ................................... 600/443, 441, 600/455–459; 73/861.25

[56] References Cited

U.S. PATENT DOCUMENTS

| | | | |
|---|---|---|---|
| 4,320,765 | 3/1982 | Cathignol et al. ....................... | 600/455 |
| 5,014,712 | 5/1991 | O'Donnell ............................... | 600/447 |
| 5,022,400 | 6/1991 | Walters .................................... | 600/455 |
| 5,363,851 | 11/1994 | Hall et al. ................................ | 600/455 |
| 5,632,277 | 5/1997 | Chapman et al. ................... | 128/660.07 |
| 5,706,819 | 1/1998 | Hwang et al. ....................... | 128/662.02 |

OTHER PUBLICATIONS

Takeuchi, "Chirped Excitation for <100dB Time Sidelobe Echo Sounding," Proc. 1995 IEEE Ultrasonics Symp., pp. 1309–1314.

Takeuchi, "Coded Excitation for Harmonics Imaging", Proc. 1996 IEEE Ultrasonics Symp., pp. 1433–1436.

Welch, "Pulse Compression Ultrasound for Minimization of Transmitted Peak Power", Proc. 20th Annual Northeast Bioengineering Conference, Springfield, MA.

Welch et al., "Sidelobe Suppressed Spread Spectrum Pulse Compression for Ultrasonic Tissue Imaging,"IEEE Trans. Ultrasonics, Ferroelec. & Freq. Control (accepted for publication 1997).

Lee et al., "High–Speed Digital Golay Code Flaw Detection System," Proc. 1981 Ultrasonics Symp., pp. 888–891.

Hayward et al., "A Digital Hardware Correlation System for Fast Ultrasonic Data Acquisition in Peak Power Limited Applications," IEEE Trans. Ultrason. Ferroelec. Freq. Cont., vol. 35, No. 6, Nov. 1988, pp. 800–808.

Mayer et al., "Three–Dimensional Imaging System Based on Fourier Transform Synthetic Aperture Focusing Technique," Ultrasonics, vol. 28, Jul. 1990, pp. 241–255.

Takeuchi, "An Investigation of a Spread Energy Method for Medical Ultrasound Systems. II. Proposed System and Possible Problems," Ultrasonic, vol. 17, Sep. 1979, pp. 219–224.

O'Donnell, "Coded Excitation System for Improving the Penetration of Real–Time Phased–Array Imaging Systems," IEEE Trans. Ultrason. Ferroelec. Freq. Cont., vol. 39, No. 3, May 1992, pp. 341–351.

*Primary Examiner*—Francis J. Jaworski
*Attorney, Agent, or Firm*—Dennis M. Flaherty; Christian G. Cabou; Phyllis Y. Price

[57] ABSTRACT

A method and an apparatus for improving the signal-to-noise ratio (SNR) and/or resolution in color flow ultrasound imaging by using complementary-coded excitation of the transducer array. The SNR is improved by transmitting a pair of Golay-coded pulse sequences in alternating sequence at the same transmit focal position over multiple firings and then partly decoding the beamsummed data. The partly decoded data is then vector summed and high pass filtered. The summed and high-pass-filtered data is optionally decimated by a factor of two. The decimated or undecimated data is then input to the parameter estimator, which provides imaging signals representing the flow in a scan plane. Those imaging signals are then displayed as color information on a display monitor.

39 Claims, 3 Drawing Sheets

METHOD AND APPARATUS FOR COLOR FLOW IMAGING USING GOLAY-CODED EXCITATION ON TRANSMIT AND PULSE COMPRESSION ON RECEIVE

FIELD OF THE INVENTION

This invention generally relates to ultrasound color flow Doppler imaging of fluid flow fields. In particular, the invention relates to a method and an apparatus for imaging blood flowing in the human body by detecting Doppler shifting of ultrasonic echoes reflected from the flowing blood.

BACKGROUND OF THE INVENTION

Ultrasonic scanners for detecting blood flow based on the Doppler effect are well known. Such systems operate by actuating an ultrasonic transducer array to transmit ultrasonic waves into the object and receiving ultrasonic echoes backscattered from the object. In the measurement of blood flow characteristics, returning ultrasonic waves are compared to a frequency reference to determine the frequency shift imparted to the returning waves by flowing scatterers such as blood cells. This frequency, i.e., phase, shift translates into the velocity of the blood flow. The blood velocity is calculated by measuring the phase shift from firing to firing at a specific range gate.

The change or shift in backscattered frequency increases when blood flows toward the transducer and decreases when blood flows away from the transducer. Color flow images are produced by superimposing a color image of the velocity of moving material, such as blood, over a black and white anatomical B-mode image. Typically, color flow mode displays hundreds of adjacent sample volumes simultaneously, all laid over a B-mode image and color-coded to represent each sample volume's velocity.

In standard color flow processing, a high pass filter known as a wall filter is applied to the data before a color flow estimate is made. The purpose of this filter is to remove signal components produced by tissue surrounding the blood flow of interest. If these signal components are not removed, the resulting velocity estimate will be a combination of the velocities from the blood flow and the surrounding tissue. The backscatter component from tissue is many times larger than that from blood, so the velocity estimate will most likely be more representative of the tissue, rather than the blood flow. In order to get the flow velocity, the tissue signal must be filtered out.

In the color flow mode of a conventional ultrasound imaging system, an ultrasound transducer array is activated to transmit a series of multi-cycle (typically 4–8 cycles) tone bursts which are focused at the same transmit focal position with the same transmit characteristics. These tone bursts are fired at a pulse repetition frequency (PRF). The PRF is typically in the kilohertz range. A series of transmit firings focused at the same transmit focal position are referred to as a "packet". Each transmit beam propagates through the object being scanned and is reflected by ultrasound scatterers such as blood cells. The return signals are detected by the elements of the transducer array and then formed into a receive beam by a beamformer.

For example, the traditional color firing sequence is a series of firings (e.g., tone bursts) along the same position, which firings produce the respective receive signals:

$$F_1\ F_2\ F_3\ F_4 \ldots F_M$$

where $F_i$ is the receive signal for the i-th firing and M is the number of firings in a packet. These receive signals are loaded into a corner turner memory, and a high pass filter (wall filter) is applied to each down range position across firings, i.e., in "slow time". In the simplest case of a (1, −1) wall filter, each range point will be filtered to produce the respective difference signals:

$$(F_1-F_2)\ (F_2-F_3)\ (F_3-F_4) \ldots (F_{M-1}-F_M)$$

and these differences are input to a color flow velocity estimator.

One of the primary advantages of Doppler ultrasound is that it can provide noninvasive and quantitative measurements of blood flow in vessels. Given the angle θ between the insonifying beam and the flow axis, the magnitude of the velocity vector can be determined by the standard Doppler equation:

$$V = cf_d/(2f_0 \cos \eta) \qquad (1)$$

where c is the speed of sound in blood, $f_0$ is the transmit frequency and $f_d$ is the motion-induced Doppler frequency shift in the backscattered ultrasound.

Because blood has a very low backscatter coefficient, in medical ultrasound color flow imaging, it is desirable to improve flow visualization by optimizing the SNR and resolution. Coded excitation is a well-known radar technique which is used in situations where the peak power of a transmitted signal cannot be increased but the average power can. This is often the case in medical ultrasound imaging, where system design limitations dictate the peak amplitude of the signal driving the transducer. Coded excitation can be used to increase signal-to-noise ratio by transmitting a longer pulse and/or to increase resolution by having a shorter decoded pulse.

In medical ultrasound imaging, longer signals, such as chirps, can be used to deliver higher average power values, and temporal resolution is restored by correlating the return signal with a matched filter. Chirps, however, are expensive to implement on a phased array ultrasound system due to the complexity of the electronics, so binary codes, or codes that can be easily represented digitally as a series of digits equal to +1, −1 or 0, are more practical. Binary codes are also preferred because they contain the most energy for a given peak amplitude and pulse duration. The problems with binary codes is that sidelobes generated in the correlation process generally degrade the image.

Acceptable sidelobe levels can be produced using a complementary set of transmit codes, e.g., Golay codes. A set of complementary-coded waveforms produce signals which, after autocorrelation and summation, yield a short pulse in range, due to the fact that the sidelobe levels produced by the autocorrelation of one code sequence are equal in magnitude but opposite in sign to the those of the complementary sequence.

There are situations where these ideas can be extended to color flow processing as well. In cases where the flow dynamics are low enough that one does not degrade the codes between the complementary firings, one can gain SNR if, again, one is limited by the system peak power but not by the average power. In addition, color flow systems already tend to fire relatively long tone bursts to maximize the SNR, so one can gain additional spatial resolution over typical Doppler processing by using coded sequences.

SUMMARY OF THE INVENTION

The present invention is a method and an apparatus for improving the SNR and/or resolution in color flow ultrasound imaging by using Golay-coded excitation on transmit and pulse compression on receive. Coded excitation allows a long transmit pulse to be compressed on receive such that most energy is concentrated in a short interval. This technique can be used to maximize color flow sensitivity in deep-lying regions. Alternatively, for a given transmit acoustic burst length and dosage, the spatial resolution can be improved without compromising sensitivity.

In accordance with the preferred embodiment of the invention, the SNR and/or resolution are improved by transmitting a pair of Golay-coded pulse sequences in alternating sequence at the same transmit focal position and then partly decoding (using a matching filter) the data after beamsumming (and before demodulation) or after both beamsumming and demodulation have occurred. The partly decoded data is then vector summed to produce the fully decoded, i.e., pulse-compressed, signals, which are then passed through a high pass filter (wall filter). The wall-filtered pulse-compressed signals are output to a velocity or power estimator which provides imaging signals representing flow in the scan plane. These imaging signals are then displayed as color information on a display monitor.

In accordance with the preferred embodiment of the invention, a pair of Golay-coded pulse sequences are generated by bipolar pulsers in response to respective Golay-coded transmit sequences. Each Golay-coded transmit sequence is derived by convolving a respective Golay code pair with a base sequence. A Golay code pair is a pair of binary (+1, −1) sequences with the property that the sum of the autocorrelations of the two sequences is a Kronecker delta function.

By transmitting two sequences of pulses (e.g., multi-cycle tone bursts) that are phase (i.e., polarity) coded in accordance with the Golay-coded transmit sequences, respectively, the correlation of each of the beamsummed or beamsummed and demodulated signals with its corresponding Golay code and the summation of those correlations enables an increase in the SNR with virtually no degradation in image resolution or contrast, or an increase in resolution with no degradation in SNR or contrast. In practice, range sidelobes occur due to tissue motion between successive transmit firings, but that degradation of the decoded signal is small for low-velocity flow.

In accordance with the broad concept of the invention, the beamformer output can be either an RF signal or its I/Q components. Preferably, the beamformer output is partially decoded, demodulated and then completely decoded. In the case of an RF beamformer output, the demodulator transforms the partly decoded RF signal into its I/Q components for color flow processing. If the demodulator precedes the decoding filter, then the decoding filter must be designed to partly decode the demodulated signals.

DETAILED DESCRIPTION OF THE PREFERRED EMBODIMENTS

Figure 1:
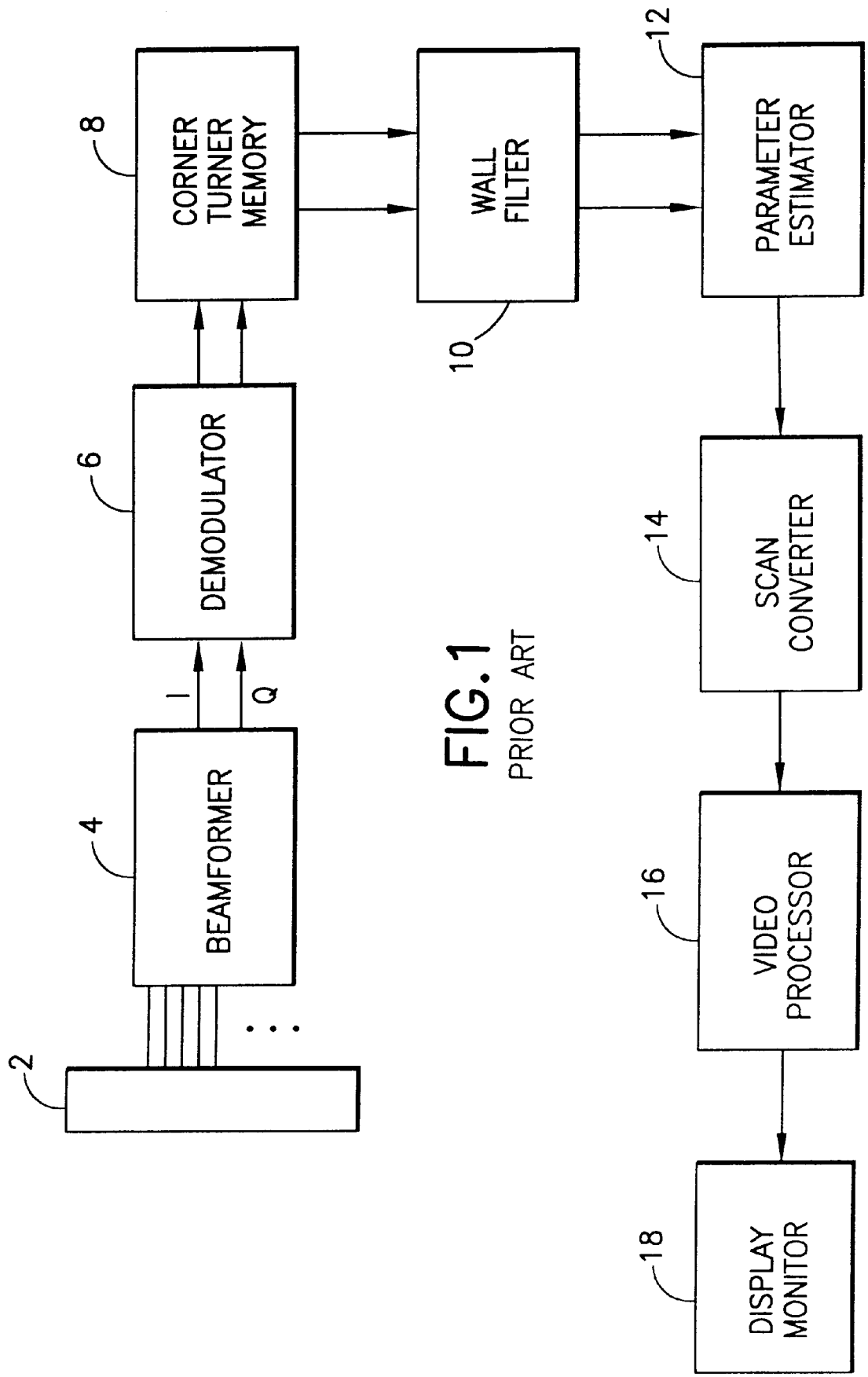
FIG. 1 is a block diagram showing the signal processing chain for a conventional color flow ultrasound imaging system.

Referring to FIG. 1, the basic signal processing chain for a color flow imaging system comprises an ultrasound transducer array 2, which is activated to transmit coded pulse sequences comprising phase-coded tone bursts of length P which are fired repeatedly at the PRF. The return RF signals are detected by the transducer elements and received by the respective receive channels in the beamformer 4. The beamformer sums the delayed channels data and outputs either RF or in-phase and quadrature (I/Q) data. The latter alternative is illustrated in FIG. 1.

In the conventional system, the frequencies of the beamformer outputs are shifted to baseband by a demodulator 6. The demodulated I/Q components are stored in a corner turner memory 8, whose purpose is to buffer data from possibly interleaved firings and output the data as vectors of points across firings at a given range cell. Data is received in "fast time", or sequentially down range (along a vector) for each firing. The output of the corner turner memory is reordered into "slow time", or sequentially by firing for each range cell. The resultant "slow time" I/Q signal samples are passed through respective wall filters 10, which reject any clutter corresponding to stationary or very slow-moving tissue. The filtered outputs are then fed into a parameter estimator 12, which converts the range cell information into the intermediate autocorrelation parameters N, D, and R(0). N and D are the numerator and denominator for the autocorrelation equation, as shown below:

$$N = \sum_{i=1}^{M-1} (I_i Q_{i+1} - I_{i+1} Q_i) \quad (2)$$

$$D = \sum_{i=1}^{M-1} (I_i I_{i+1} - Q_i Q_{i+1}) \quad (3)$$

where $I_i$ and $Q_i$ are the demodulated, basebanded input data for firing i, and M is the number of firings in the packet. R(0) is approximated as a finite sum over the number of firings in a packet, as follows:

$$R(0) = \sum_{i=1}^{M-1} \frac{(I_i^2 + Q_i^2 + I_{i+1}^2 + Q_{i+1}^2)}{2} \quad (4)$$

A processor converts N and D into a magnitude and phase for each range cell. The equations used are as follows:

$$|R(T)| = \sqrt{N^2 + D^2} \quad (5)$$

$$\phi(R(T)) = \tan^{-1}\left[\frac{N}{D}\right] \quad (6)$$

The parameter estimator processes the magnitude and phase values into estimates of power, velocity and turbulence. The phase is used to calculate the mean Doppler frequency, which is proportional to the velocity as shown below; R(0) and |R(T)| (magnitude) are used to estimate the turbulence.

The mean Doppler frequency in hertz is obtained from the phase of N and D and the pulse repetition time T:

$$\bar{f} = \frac{1}{2\pi T} \tan^{-1}\left[\frac{N}{D}\right] = \frac{1}{2\pi T}(\phi(R(T))) \quad (7)$$

The mean velocity is calculated using the Doppler shift equation below. Since θ, the angle between the flow direction and the sampling direction, is not known, cos θ is assumed to be 1.0.

$$\overline{v} = \frac{\overline{f}}{f_0} \frac{c}{2\cos\theta} \qquad (8)$$

Note that the parameter estimator does not calculate the mean Doppler frequency as an intermediate output, but calculates $\overline{v}$ directly from the phase output of the processor using a look-up table.

The turbulence may be calculated in the time domain as a second-order series expansion of the variance of the mean Doppler frequency. The time domain expression for turbulence involves calculating the zero-lag and one-lag autocorrelation functions, R(0) and R(T) respectively. The exact autocorrelation functions are approximated by finite sums over the known data in the number of firings in a packet:

$$\sigma^2 = \frac{2}{(2\pi T)^2}\left[1 - \frac{|R(T)|}{R(0)}\right] \qquad (9)$$

The mean value signal $\phi(R(T))$ is an estimate of the mean Doppler frequency shift of the flowing reflectors, which in turn is proportional to the mean blood flow velocity. The variance signal $\sigma^2$ indicates the frequency spread of the flow signal component of the baseband echo signal. This value is indicative of flow turbulence, since laminar flow has a very narrow range of velocities, while turbulent flow is a mixture of many velocities. To indicate the strength of the signal from the flowing reflectors, the signal R(0) indicates the amount of the returned power in the Doppler-shifted flow signal.

The color estimates are sent to a scan converter 14, which converts the color images into X-Y format for video display. The scan-converted frames are passed to a video processor 16, which basically maps the video data to a display color map for video display. The color flow image frames are then sent to the video monitor 18 for display. Typically, either velocity or power are displayed alone or velocity is displayed in conjunction with either power or turbulence. System control is centered in a host computer (not shown), which accepts operator inputs through an operator interface (e.g., a keyboard) and in turn controls the various subsystems.

Figure 2:
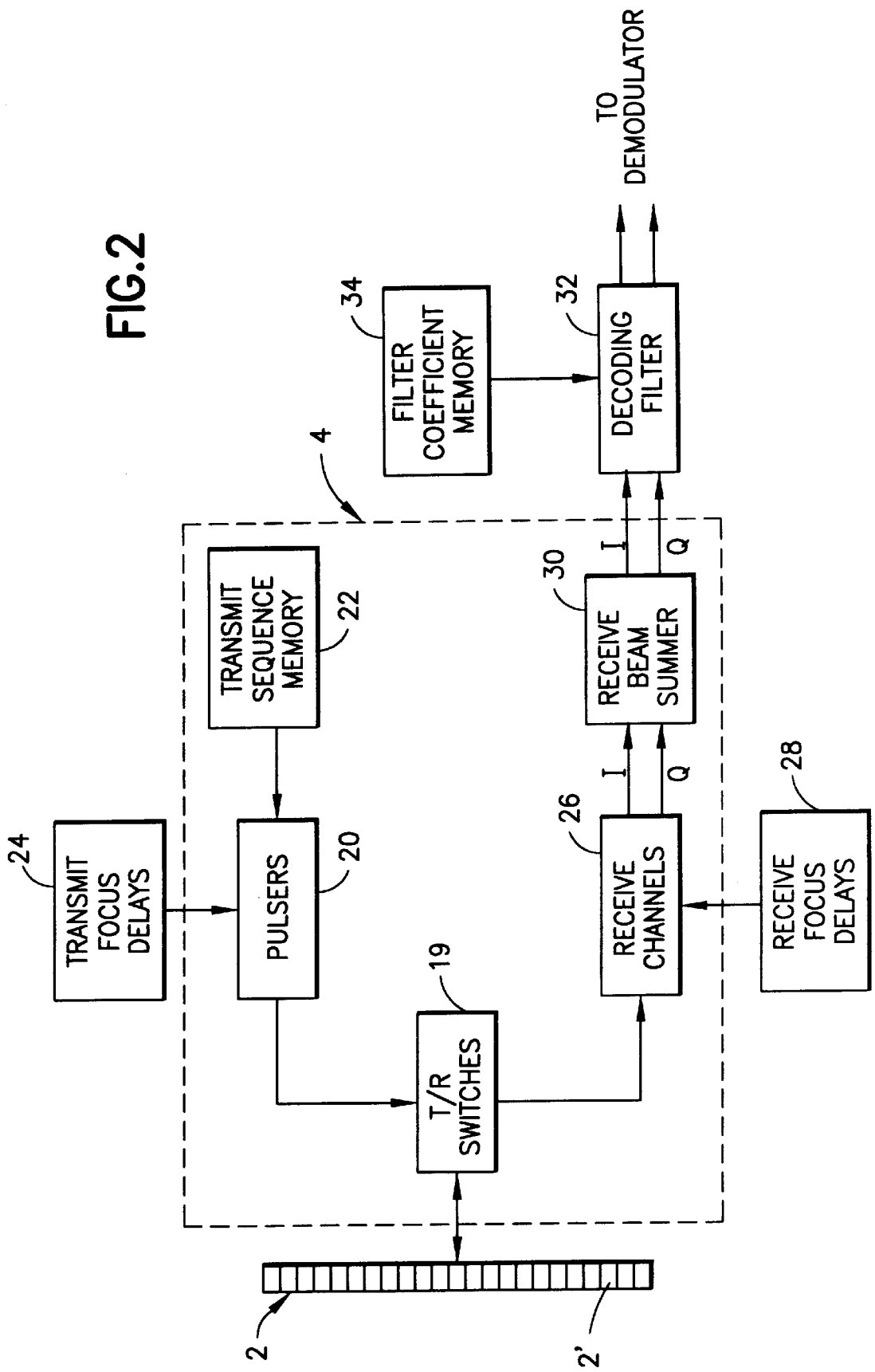
FIG. 2 is a block diagram showing the front end of a color flow ultrasound imaging system in accordance with a preferred embodiment of the invention.

The preferred embodiment of the invention is shown in FIG. 2. For each transmit firing, each transducer element 2' in the transmit aperture is pulsed with a coded pulse sequence output by a respective bipolar pulser 20. The coded pulse sequence is derived from a coded transmit sequence formed by convolving a transmit code (e.g., a Golay code) with a base sequence (e.g., a multi-cycle tone burst). For an n-digit transmit code, the coded pulse sequence comprises n chips. In accordance with the preferred embodiments of the invention, the bipolar pulsers generate a polarity-coded pulse sequence in which the phase of pulses encoded with a +1 is 0°, while the phase of pulses encoded with a −1 is 180°. The coded transmit sequence for controlling the phase of pulses output by each bipolar pulser 20 is stored in a transmit sequence memory 22.

The bipolar pulsers 20 drive the elements 2' of transducer array 2 such that the ultrasonic energy produced is focused in a beam for each transmit firing. To accomplish this, transmit focus time delays 24 are imparted to the respective pulsed waveforms output by the pulsers in response to the coded transmit sequence. By appropriately adjusting the transmit focus time delays in a conventional manner, the ultrasonic beam can be focused at a desired transmit focal position. The coded pulse sequences are sent from the pulsers to the transducer elements via respective transmit/receive (T/R) switches 19. The T/R switches 19 are typically diodes which protect the receive electronics from the high voltages generated by the transmit electronics. The transmit signal causes the diodes to shut off or limit the signal to the receiver.

After each transmit, the transducer elements 2' are switched to receive mode to accept the returning echoes backscattered from the object being scanned These return signals are fed to respective receive channels 26 of the receive beamformer, also via the T/R switches 19. The receive beamformer tracks echoes under the direction of a master controller (not shown). The receive beamformer imparts the proper receive focus time delays 28 to the received echo signal and sums them to provide an echo signal which accurately indicates the total ultrasonic energy reflected from a succession of ranges corresponding to a particular transmit focal position. In accordance with the embodiment depicted in FIG. 2, the beamformer also transforms the RF signal into its I/Q components by means of Hilbert bandpass filtering in each receive channels. The I/Q components are then summed in receive summer 30 for each transmit firing. Hilbert bandpass filtering can alternatively be performed after beam summation.

The I/Q components for each transmit firing are then matched filtered by a respective decoding filter 32 which outputs a partly decoded pulse in accordance with the present invention. For an n-digit transmit code, the decoding filter 32 is preferably an FIR filter having n filter taps for receiving a set of n filter coefficients from a filter coefficient memory 34. In accordance with a preferred embodiment, the filter coefficients $c_0, c_1, \ldots, C_{n-1}$ have scalar values which, when convolved with the n-digit transmit code and then summed with the complementary signal, produce a partly decoded pulse sequence. [The filter coefficients, like the transmit and receive time delays and the coded transmit sequences, can be supplied by the master controller.] The appropriate decoding filter is designed based on the transmit code, the demodulation frequency (if decoding follows demodulation) and the amount of downsampling performed on receive.

The ultrasound imaging system shown in FIG. 3 employs complementary code processing for color flow imaging as follows. Instead of transmitting a packet consisting of M transmit firings (e.g., each pulse being a multi-cycle tone burst), one would transmit a packet consisting of 2M transmit firings, successive transmit pulses being alternatingly encoded with the respective codes of the complementary (e.g., Golay) code pair to form alternating coded pulse sequences A and B. For example, coded pulse sequence A could be formed by coding a sequence of n transmit pulse sequences with respective digits of a first n-digit transmit code and coding another sequence of n transmit pulse sequences with respective digits of a second n-digit transmit code, wherein the first and second transmit codes are complementary. The autocorrelation is achieved for each transmit firing by loading decoding filter 32 with a receive code equal to the transmit code for that firing and then performing matched filtering of the receive signals. The autocorrelated sequences are then summed using respective dedicated vector summers 36 and high pass filtered using respective wall filters 10. Alternatively, the dual functions of summing Golay code pairs and high pass filtering can be performed by respective "generalized" wall filters. A generalized wall filter is formed by duplicating the filter coefficients of a conventional wall filter. The summed and high-pass-filtered data is optionally decimated by a factor of two in respective decimators 38. The decimated or undecimated data is then input to the parameter estimator 12.

In accordance with a preferred embodiment of the invention, the beamformer 4 fires a packet of complementary coded pulse sequences A and B in alternating sequence, i.e., A B A B . . . The receive signals resulting from this packet can be designated as follows:

$$A_1 \; B_1 \; A_2 \; B_2 \; A_3 \; B_3 \ldots A_M \; B_M$$

where $A_i$ is the receive signal for the i-th firing of code A, $B_i$ is the receive signal for the i-th firing of code B, which is the complement of code A, and 2M is the number of firings in a packet.

From this point, there are two cases which must be considered. The first case is where the pulse repetition interval (PRI) can be defined as the time between an A firing and the next B firing (every firing is separated by some time, PRI). This PRI time is such that there is adequate receive signal correlation between the A firings and B firings to perform vector summation of the complementary codes and achieve adequate sidelobe cancellation and peak signal integration, but also enough decorrelation between the firings to allow for adequate parameter estimation. The PRF in this case is the frequency at which each individual firing is fired.

In this first case, where the PRF is the frequency at which the complementary-coded pulse sequences are fired, the I/Q components of the receive signals are loaded into corner turner memory 8. A vector summation of the successive A and B firings is performed. This can be accomplished in either of two ways. Either a dedicated summer can be implemented or the wall filter can be used to effectively perform the vector summation and wall filtering functions at the same time.

If a dedicated vector summer 36 (see FIG. 3) is used, then the dedicated summer is applied to each down range position across the alternate firings in "slow time" such that the output samples of the dedicated summer for each down range position are:

$$(A_1+B_1) \; (B_1+A_2) \; (A_2+B_2) \; (B_2+A_3) \ldots (B_{M-1}+A_M) \; (A_M+B_M)$$

In this way, the number of samples into the dedicated summer 36 is 2 M and the number samples out of the dedicated summer is (2M−1). A wall filter 10 is then applied to the (2M−1) summed samples for each down range position, again in "slow time". In the simplest case of a (1, 0, −1) wall filter, each range point will be filtered to produce the following respective difference signals while also preserving the previous summation:

$$(A_1 + B_1) - (A_2 + B_2)$$

$$(B_1 + A_2) - (B_2 + A_3)$$

$$(A_2 + B_2) - (A_3 + B_3)$$

$$(B_2 + A_3) - (B_3 + A_4)$$

$$\ldots$$

$$(A_{M-1} + B_{M-1}) - (A_M + B_M)$$

(Parentheses have been inserted to make the mathematics more obvious.) If the generalized wall filter is used to perform both the vector summation and wall filtering functions, then the generalized wall filter is applied to each down range position across firings in "slow time". The generalized wall filter is formed by duplicating the filter coefficients of a conventional wall filter. In the simplest case of a conventional (1, −1) wall filter, the generalized wall filter will have filter coefficients (1, 1, −1, −1). In this case, each range point will be filtered to produce the respective difference signals:

$$(A_1 + B_1) - (A_2 + B_2)$$

$$(B_1 + A_2) - (B_2 + A_3)$$

$$(A_2 + B_2) - (A_3 + B_3)$$

$$(B_2 + A_3) - (B_3 + A_4)$$

$$\ldots$$

$$(A_{M-1} + B_{M-1}) - (A_M + B_M)$$

From the above, it can be seen that adjacent complementary code sequences are added (vector summed) together, and these vector sums are then high pass filtered (wall filtered). This is the same result as achieved in the previous situation where the summation is performed separately and before wall filtering. Even though two coded pulse sequences are required for each transmit firing, because of the staggering of the coded pulse sequences, the total number of firings in the packet only needs to be increased by the number of additional wall filter taps to obtain the equivalent number of samples out of the wall filter and into the parameter estimator. Thus, frame rates can be kept sufficiently high by using relatively short wall filters. Again, this implementation has the PRI defined as the time between A and B firings (each firing) and the PRF is the frequency at which the complementary-coded pulse sequences are fired.

The second case is where the PRI can be defined as the time interval between successive A firings (or successive B firings) and the time interval between an A firing and the next B firing is essentially the round trip travel time, which is shorter than the PRI. This case assumes that there is no correlation between successive A firings (or successive B firings) so adequate parameter estimation can be performed. However, there is sufficient receive signal correlation between an A firing and the next B firing because the round trip travel time between the A firing and the next B firing is small enough to maintain good correlation between these firings for sidelobe cancellation and peak signal integration. In this second case, the PRF is the frequency at which the individual coded pulse sequences A or B are fired. Again, the PRI between successive A firings and between successive B firings is adequate for parameter estimation.

Again, the I/Q components of the receive signals are loaded into corner turner memory 8. The dedicated vector summer 36 can be used in conjunction with a conventional wall filter 10, or a separate dedicated vector summer need not be used and the wall filter can be generalized to perform both summation and wall filtering. The resultant samples out of the wall filter, based on the example above, is again the same as in the first case. However, not all of these samples will be presented to the parameter estimator in this case. Every other difference signal must be removed by a decimator 38 (see FIG. 3) because those signals [e.g., $(B_1+A_2)-(B_2+A_3)$] have summations which are not correlated sufficiently to yield adequate sidelobe cancellation and peak signal integration. As a result, fewer samples are available for parameter estimation in this second case and packet size would need to be increased to restore the number of samples into the parameter estimator obtained in the first case.

To implement coded excitation on a digital ultrasound scanner, the encoding on transmit can be realized simply by convolving the respective complementary transmit code with the desired base sequence (e.g., [1, —1,1, −1]). For example, for odd-numbered transmit firings, the transducer elements are driven with a coded pulse sequence A output by the bipolar pulsers in response to a coded transmit sequence [1,−1,1, −1] [1,−1,1, −1], derived by convolving the Golay code [1,1] with the base sequence [1, −1,1, −1]. On receive, the beam-summed signals are partly decoded via respective decoding FIR filters whose coefficients are matched to the Golay code [1,1]. Similarly, for even-numbered transmit firings, the transducer elements are driven with a coded pulse sequence B output by the bipolar pulsers in response to a coded transmit sequence [1, −1,1, −1] [−1,1, −1,1], derived by convolving the Golay code [1, −1] with the base sequence [1, −1,1, −1]. On receive, the beamsummed signals are partly decoded via the respective decoding FIR filters whose coefficients are matched to the Golay code [1, −1].

The decoding filters 32 (see FIG. 3) output the respective partly decoded pulse sequences to the demodulator 6. These decoded I/Q signals are shifted in frequency by demodulator 6. One way of achieving this is to multiply the input signal by a complex sinusoidal $e^{i2\pi f d r}$, where $f_d$ is the frequency shift required to bring the signal spectrum to baseband. The vector summers 36 receive the partly decoded pulse sequences and vector sum them to form the fully decoded, i.e., pulse-compressed, signals. The wall filters 10 then subtract the pulse-compressed signals to form wall-filtered pulse-compressed signals. Optionally the wall filter output is decimated. The decimated or undecimated wall-filtered pulse-compressed signals are then used in parameter estimation.

Figure 3:
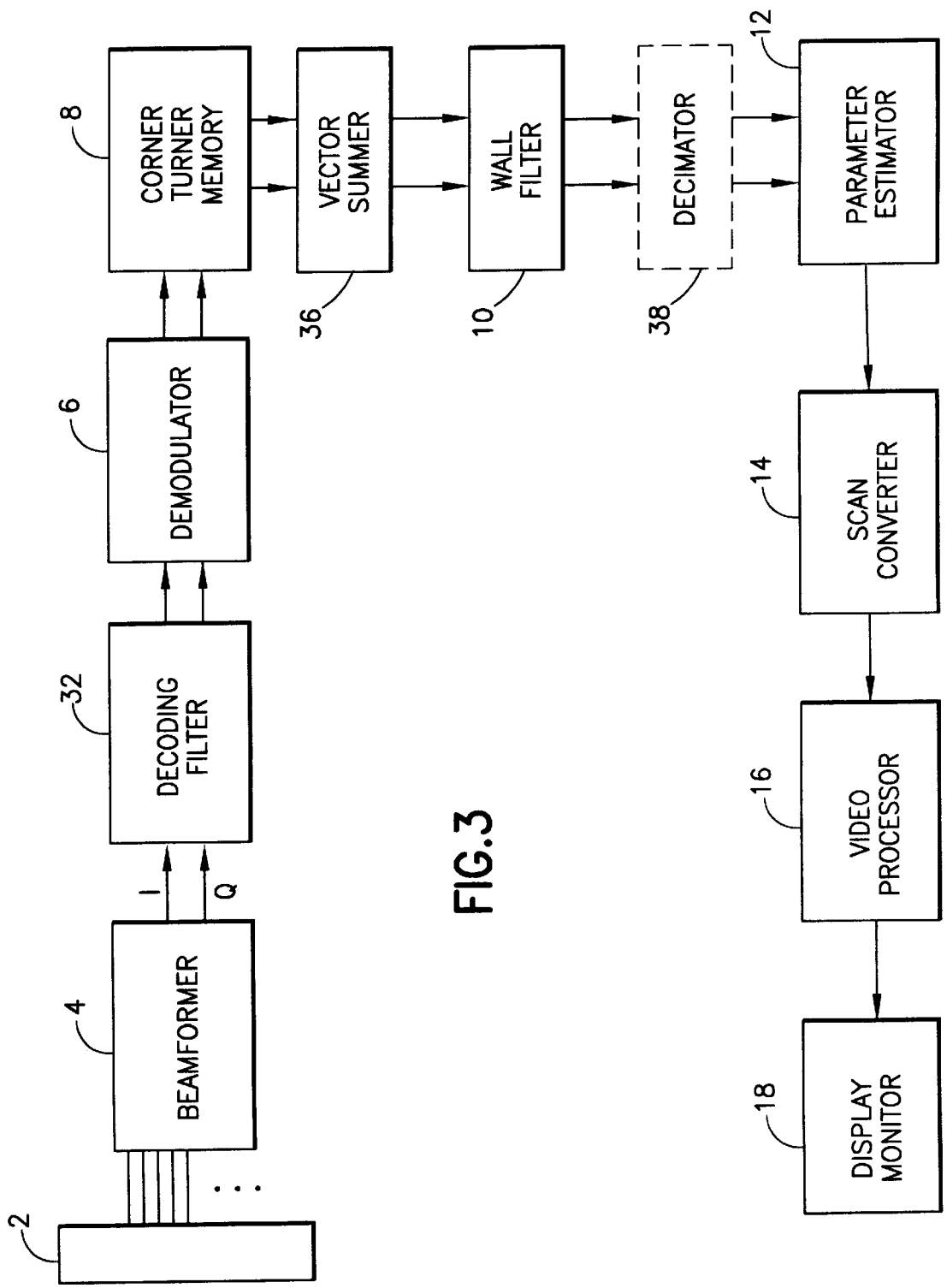
FIG. 3 is a block diagram showing the signal processing chain for a color flow ultrasound imaging system in accordance with the preferred embodiment shown in FIG. 2.

The decoding FIR filters 32 can be implemented in software or hardware at the beamformer output, as shown in FIG. 3, or at the demodulator output (not shown). In the latter case, the decoding filter coefficients must be matched to the demodulated signals. For the case when the demodulator shifts by discrete frequencies $f_d = k/2t_b$, where k is any positive integer and $t_b$ is the duration of the transmit base sequence, the sinusoidal becomes real and the same set of filter coefficients are input to both decoding filters for the I and Q components, which thus form a real filter. In the cases when $f_d \neq k/2t_b$, the I and Q decoding filters receive different sets of filter coefficients and thus form a complex filter. In the latter case, the filter coefficients are matched to the respective demodulated signal component.

The foregoing preferred embodiments have been disclosed for the purpose of illustration. Variations and modifications of the concept of the invention will be readily apparent to persons skilled in the art. In particular, the transmit pulse sequences may be amplitude-coded, rather than phase- or polarity-coded. In addition, polyphase codes can be used in place of biphase codes. All such variations and modifications are intended to be encompassed by the claims set forth hereinafter.

We claim:

1. A system for imaging flow of ultrasound scatterers, comprising:
    an ultrasound transducer array comprising a multiplicity of transducer elements;
    transmit means coupled to said transducer array for pulsing a set of selected transducer elements which form a transmit aperture with a first coded pulse sequence during first and third transmit firings and with a second coded pulse sequence during second and fourth transmit firings, said first through fourth transmit firings being focused at substantially the same transmit focal position, said first coded pulse sequence being a function of a first transmit code convolved with a base pulse sequence, said second coded pulse sequence being a function of a second transmit code convolved with said base pulse sequence, and said first and second transmit codes being complementary;
    acquisition means coupled to said transducer array for acquiring first through fourth beamsummed signals subsequent to said first through fourth transmit firings respectively;
    means for matched filtering said first and third beamsummed signals using a first set of filter coefficients which match said first transmit code to form first and third partly decoded signals and matched filtering said second and fourth beamsummed signals using a second set of filter coefficients which match said second transmit code to form second and fourth partly decoded signals;
    means for forming a first signal representing a difference between a sum of said first and second partly decoded signals and a sum of said third and fourth partly decoded signals;
    means for estimating a flow parameter as a function of at least said first signal to form a flow image signal; and
    means for displaying an image which is a function of said flow image signal.

2. The system as defined in claim 1, wherein said flow parameter is power.

3. The system as defined in claim 1, wherein:
    said transmit means pulse said set of selected transducer elements which form said transmit aperture with said first coded pulse sequence during a fifth transmit firing, said fifth transmit firing being focused at substantially said same transmit focal position;
    said acquisition means form a fifth beamsummed signal subsequent to said fifth transmit firing;
    said matched filtering means filter said fifth beamsummed signal using said first set of filter coefficients to form a fifth partly decoded signal;
    said forming means form a second signal representing a difference between a sum of said second and third partly decoded signals and a sum of said fourth and fifth partly decoded signals; and
    said flow parameter estimating means estimate said flow parameter as a function of at least said first and second signals to form said flow image signal.

4. The system as defined in claim 3, wherein said flow parameter is velocity.

5. The system as defined in claim 3, wherein said flow parameter is variance.

6. The system as defined in claim 1, wherein said forming means comprise:
    means for vector summing said first and second partly decoded signals to form a first pulse-compressed signal and vector summing said third and fourth partly decoded signals to form a second pulse-compressed signal; and
    a high pass filter for high pass filtering said first and second pulse-compressed signals to form said first signal.

7. The system as defined in claim 1, wherein said forming means comprise a generalized wall filter.

8. The system as defined in claim 7, wherein said generalized wall filter has filter coefficients [1,1, −1, −1].

9. The system as defined in claim 1, wherein said forming means comprises a wall filter having filter coefficients [1,0, −1].

10. The system as defined in claim 1, wherein said first and second transmit codes form a Golay code pair.

11. A system for imaging flow of ultrasound scatterers, comprising:

an ultrasound transducer array comprising a multiplicity of transducer elements;

transmit means coupled to said transducer array for pulsing a set of selected transducer elements which form a transmit aperture with a first coded pulse sequence during first and third transmit firings and with a second coded pulse sequence during second and fourth transmit firings, said first through fourth transmit firings being focused at substantially the same transmit focal position, said first coded pulse sequence being a function of a first transmit code convolved with a base pulse sequence, said second coded pulse sequence being a function of a second transmit code convolved with said base pulse sequence, and said first and second transmit codes being complementary;

acquisition means coupled to said transducer array for acquiring first through fourth beamsummed signals subsequent to said first through fourth transmit firings respectively;

means for matched filtering said first and third beamsummed signals using a first set of filter coefficients which match said first transmit code to form first and third partly decoded signals and matched filtering said second and fourth beamsummed signals using a second set of filter coefficients which match said second transmit code to form second and fourth partly decoded signals;

means for forming a first wall-filtered pulse-compressed signal from said first through fourth partly decoded signals;

means for estimating a flow parameter as a function of at least said first wall-filtered pulse-compressed signal to form a flow image signal; and means for displaying an image which is a function of said flow image signal.

12. The system as defined in claim 11, wherein said flow parameter is power.

13. The system as defined in claim 11, wherein:

said transmit means pulse said set of selected transducer elements which form said transmit aperture with said first coded pulse sequence during a fifth transmit firing and with a second coded pulse sequence during a sixth transmit firing, said fifth and sixth transmit firings being focused at substantially said same transmit focal position;

said acquisition means form fifth and sixth beamsummed signals subsequent to said fifth and sixth transmit firings respectively;

said matched filtering means filter said fifth beamsummed signal using said first set of filter coefficients to form a fifth partly decoded signal and filters said sixth beamsummed signal using said second set of filter coefficients to form a sixth partly decoded signal;

said forming means form a second wall-filtered pulse-compressed signal from said third through sixth partly decoded signals; and said flow parameter estimating means estimate said flow parameter as a function of at least said first and second wall-filtered pulse-compressed signals to form said flow image signal.

14. The system as defined in claim 13, wherein said flow parameter is velocity.

15. The system as defined in claim 13, wherein said flow parameter is variance.

16. The system as defined in claim 11, wherein said forming means comprise:

means for vector summing said first and second partly decoded signals to form a first pulse-compressed signal and vector summing said third and fourth partly decoded signals to form a second pulse-compressed signal; and a high pass filter for high pass filtering said first and second pulse-compressed signals to form said first wall-filtered pulse-compressed signal.

17. The system as defined in claim 11, wherein said forming means comprise a generalized wall filter.

18. The system as defined in claim 17, wherein said generalized wall filter has filter coefficients [1,1,−1,−1].

19. The system as defined in claim 11, wherein said forming means comprises a wall filter having filter coefficients [1,0, −1].

20. The system as defined in claim 11, wherein said first and second transmit codes form a Golay code pair.

21. The system as defined in claim 11, further comprising a decimator arranged between said forming means and said flow parameter estimating means.

22. A method for imaging ultrasound scatterers, comprising the steps of:

producing a first coded pulse sequence which is a function of a first transmit code convolved with a base pulse sequence and a second coded pulse sequence which is a function of a second transmit code convolved with said base pulse sequence, said first and second transmit codes being complementary;

driving transducer elements with said first coded pulse sequence during a first transmit firing, with said second coded pulse sequence during a second transmit firing, with said first coded pulse sequence during a third transmit firing, and with said second coded pulse sequence during a fourth transmit firing, said first through fourth transmit firings being focused at a transmit focal position;

receiving a first through fourth sets of echo signals from transducer elements subsequent to said first through fourth transmit firings respectively;

forming first through fourth beamsummed signals derived from said first through fourth sets of echo signals respectively;

matched filtering said first and third beamsummed signals using a first set of filter coefficients which match said first transmit code to form first and third partly decoded signals respectively;

matched filtering said second and fourth beamsummed signal using a second set of filter coefficients which match said second transmit code to form second and fourth partly decoded signals;

forming a first signal representing a difference between a sum of said first and second partly decoded signals and a sum of said third and fourth partly decoded signals;

estimating a flow parameter as a function of at least said first signal to form a flow image signal; and displaying an image which is a function of said flow image signal.

23. The method as defined in claim 22, wherein said flow parameter is power.

24. The method as defined in claim 22, further comprising the steps of:

driving transducer elements with said first coded pulse sequence during a fifth transmit firing, said fifth transmit firing being focused at said transmit focal position;

receiving a fifth set of echo signals from said second set of transducer elements forming said receive aperture subsequent to said fifth transmit firing;

forming a fifth beamsummed signal derived from said fifth set of echo signals;

matched filtering said fifth beamsummed signal using said first set of filter coefficients to form a fifth partly decoded signal;

forming a second signal representing a difference between a sum of said second and third partly decoded signals and a sum of said fourth and fifth partly decoded signals; and estimating a flow parameter as a function of at least said first and second signals to form said flow image signal.

25. The method as defined in claim 24, wherein said flow parameter is velocity.

26. The method as defined in claim 24, wherein said flow parameter is variance.

27. The method as defined in claim 22, wherein said first and second transmit codes form a Golay code pair.

28. The method as defined in claim 22, further comprising the steps of:

driving transducer elements with said first coded pulse sequence during a fifth transmit firing and with said second coded pulse sequence during a sixth transmit firing, said fifth and sixth transmit firings being focused at said transmit focal position;

receiving fifth and sixth sets of echo signals from said second set of transducer elements forming said receive aperture subsequent to said fifth and sixth transmit firings respectively;

forming fifth and sixth beamsummed signal derived from said fifth and sixth sets of echo signals;

matched filtering said fifth beamsummed signal using said first set of filter coefficients to form a fifth partly decoded signal;

matched filtering said sixth beamsummed signal using said second set of filter coefficients to form a sixth partly decoded signal;

forming a second signal representing a difference between a sum of said third and fourth partly decoded signals and a sum of said fifth and sixth partly decoded signals;

estimating a flow parameter as a function of at least said first and second signals to form said flow image signal.

29. A method for imaging ultrasound scatterers, comprising the steps of:

producing a first coded pulse sequence which is a function of a first transmit code convolved with a base pulse sequence and a second coded pulse sequence which is a function of a second transmit code convolved with said base pulse sequence, said first and second transmit codes being complementary;

driving transducer elements with said first coded pulse sequence during a first transmit firing, with said second coded pulse sequence during a second transmit firing, with said first coded pulse sequence during a third transmit firing, and with said second coded pulse sequence during a fourth transmit firing, said first through fourth transmit firings being focused at a transmit focal position;

receiving a first through fourth sets of echo signals from transducer elements subsequent to said first through fourth transmit firings respectively;

forming first through fourth beamsummed signals derived from said first through fourth sets of echo signals respectively;

matched filtering said first and third beamsummed signals using a first set of filter coefficients which match said first transmit code to form first and third partly decoded signals respectively;

matched filtering said second and fourth beamsummed signals using a second set of filter coefficients which match said second transmit code to form second and fourth partly decoded signals respectively;

vector summing said first and second partly decoded signals to form a first pulse-compressed signal;

vector summing said third and fourth partly decoded signals to form a second pulse-compressed signal;

high pass filtering said first and second pulse-compressed signals to form a first wall-filtered pulse-compressed signal;

estimating a flow parameter as a function of at least said first wall-filtered pulse-compressed signal to form a flow image signal; and displaying an image which is a function of said flow image signal.

30. The method as defined in claim 29, wherein said first and third transmit firings are separated by a pulse repetition interval, said second and fourth transmit firings are separated by said pulse repetition interval, and said first and second transmit firings are separated by a round trip travel time interval less than said pulse repetition interval.

31. The method as defined in claim 29, wherein said flow parameter is power.

32. The method as defined in claim 29, further comprising the steps of:

driving transducer elements with said first coded pulse sequence during a fifth transmit firing and with said second coded pulse sequence during a sixth transmit firing, said fifth and sixth transmit firings being focused at said transmit focal position;

receiving fifth and sixth sets of echo signals from said second set of transducer elements forming said receive aperture subsequent to said fifth and sixth transmit firings respectively;

forming fifth and sixth beamsummed signals derived from said fifth and sixth sets of echo signals respectively;

matched filtering said fifth beamsummed signal using said first set of filter coefficients to form a fifth partly decoded signal;

matched filtering said sixth beamsummed signal using said second set of filter coefficients to form a sixth partly decoded signal;

vector summing said fifth and sixth partly decoded signals to form a third pulse-compressed signal;

high pass filtering said second and third pulse-compressed signals to form a second wall-filtered pulse-compressed signal;

estimating a flow parameter as a function of at least said first and second wall-filtered pulse-compressed signals to form said flow image signal.

33. The method as defined in claim 32, wherein said flow parameter is velocity.

34. The method as defined in claim 32, wherein said flow parameter is variance.

35. The method as defined in claim 29, wherein said first and second transmit codes form a Golay code pair.

36. A system for imaging flow of ultrasound scatterers, comprising:

an ultrasound transducer array comprising a multiplicity of transducer elements;

transmit means coupled to said transducer array for pulsing a set of selected transducer elements which form a transmit aperture with a first coded pulse sequence during first and third transmit firings and with a second coded pulse sequence during second and fourth transmit firings, said first through fourth transmit firings being focused at substantially the same transmit focal position, said first coded pulse sequence being a function of a first transmit code convolved with a base pulse sequence, said second coded pulse sequence being a function of a second transmit code convolved with said base pulse sequence, and said first and second transmit codes being complementary;

acquisition means coupled to said transducer array for acquiring first through fourth beamsummed signals subsequent to said first through fourth transmit firings respectively;

demodulation means for demodulating said first through fourth beamsummed signals to form first through fourth demodulated signals respectively;

means for matched filtering said first and third demodulated signals using a first set of filter coefficients which match said first transmit code to form first and third partly decoded signals and matched filtering said second and fourth demodulated signals using a second set of filter coefficients which match said second transmit code to form second and fourth partly decoded signals;

means for forming a first signal representing a difference between a sum of said first and second partly decoded signals and a sum of said third and fourth partly decoded signals;

means for estimating a flow parameter as a function of at least said first signal to form a flow image signal; and means for displaying an image which is a function of said flow image signal.

37. A system for imaging flow of ultrasound scatterers, comprising:

an ultrasound transducer array comprising a multiplicity of transducer elements;

transmit means coupled to said transducer array for pulsing a set of selected transducer elements which form a transmit aperture with a first coded pulse sequence during first and third transmit firings and with a second coded pulse sequence during second and fourth transmit firings, said first through fourth transmit firings being focused at substantially the same transmit focal position, said first coded pulse sequence being a function of a first transmit code convolved with a base pulse sequence, said second coded pulse sequence being a function of a second transmit code convolved with said base pulse sequence, and said first and second transmit codes being complementary;

acquisition means coupled to said transducer array for acquiring first through fourth beamsummed signals subsequent to said first through fourth transmit firings respectively;

demodulation means for demodulating said first through fourth beamsummed signals to form first through fourth demodulated signals respectively;

means for matched filtering said first and third demodulated signals using a first set of filter coefficients which match said first transmit code to form first and third partly decoded signals and matched filtering said second and fourth demodulated signals using a second set of filter coefficients which match said second transmit code to form second and fourth partly decoded signals;

means for forming a first wall-filtered pulse-compressed signal from said first through fourth partly decoded signals;

means for estimating a flow parameter as a function of at least said first wall-filtered pulse-compressed signal to form a flow image signal; and means for displaying an image which is a function of said flow image signal.

38. The system as defined in claim 1, wherein:

said transmit means pulse said set of selected transducer elements which form said transmit aperture with said first coded pulse sequence during a fifth transmit firing and with said second coded pulse sequence during a sixth transmit firing, said fifth and sixth transmit firings being focused at substantially said same transmit focal position;

said acquisition means form fifth and sixth beamsummed signals subsequent to said fifth and sixth transmit firings respectively;

said matched filtering means filter said fifth beamsummed signal using said first set of filter coefficients to form a fifth partly decoded signal and filter said sixth beamsummed signal using said second set of filter coefficients to form a sixth partly decoded signal;

said forming means form a second signal representing a difference between a sum of said third and fourth partly decoded signals and a sum of said fifth and sixth partly decoded signals; and said flow parameter estimating means estimate said flow parameter as a function of at least said first and second signals to form said flow image signal.

39. The system as defined in claim 38, further comprising a decimator arranged between said forming means and said flow parameter estimating means.

* * * * *